(12) United States Patent
Gritzman et al.

(10) Patent No.: US 11,496,802 B2
(45) Date of Patent: Nov. 8, 2022

(54) MEDIA STREAM DELIVERY

(71) Applicant: International Business Machines Corporation, Armonk, NY (US)

(72) Inventors: Ashley D. Gritzman, Johannesburg (ZA); Toby Kurien, Midrand (ZA); Naweed Aghmad Khan, Johannesburg (ZA); Ismail Yunus Akhalwaya, Emmarentia (ZA); Komminist Weldemariam, Ottawa (ZA)

(73) Assignee: International Business Machines Corporation, Armonk, NY (US)

( * ) Notice: Subject to any disclaimer, the term of this patent is extended or adjusted under 35 U.S.C. 154(b) by 42 days.

(21) Appl. No.: 16/699,458

(22) Filed: Nov. 29, 2019

(65) Prior Publication Data
US 2021/0168450 A1   Jun. 3, 2021

(51) Int. Cl.
| | |
|---|---|
| *H04N 21/45* | (2011.01) |
| *H04N 21/258* | (2011.01) |
| *A61B 5/16* | (2006.01) |
| *H04N 21/466* | (2011.01) |
| *H04N 21/442* | (2011.01) |

(52) U.S. Cl.
CPC ......... *H04N 21/4532* (2013.01); *A61B 5/165* (2013.01); *H04N 21/25891* (2013.01); *H04N 21/44222* (2013.01); *H04N 21/4668* (2013.01)

(58) Field of Classification Search
CPC ......... H04N 21/4532; H04N 21/44222; H04N 21/4668; H04N 21/25891; A61B 5/165
See application file for complete search history.

(56) References Cited

U.S. PATENT DOCUMENTS

| | | | |
|---|---|---|---|
| 6,585,521 B1 | 7/2003 | Obrador | |
| 10,091,554 B1 | 10/2018 | Newell et al. | |
| 10,171,877 B1 | 1/2019 | Shah et al. | |
| 10,911,829 B2 * | 2/2021 | el Kaliouby | ....... G06Q 30/0631 |
| 2013/0283162 A1 * | 10/2013 | Aronsson | ............ G11B 27/105 715/719 |
| 2013/0283303 A1 | 10/2013 | Moon et al. | |
| 2014/0164507 A1 | 6/2014 | Tesch et al. | |
| 2014/0298364 A1 | 10/2014 | Stepanov et al. | |

(Continued)

OTHER PUBLICATIONS

M. Eirinaki, et al., "Recommender Systems for Large-Scale Social Networks: A review of challenges and solutions." Future Generation Computer Systems. 78. pp. 413-418. Sep. 2017. 10.1016/j.future.2017.09.015.

(Continued)

*Primary Examiner* — Nathan J Flynn
*Assistant Examiner* — Christine A Kurien
(74) *Attorney, Agent, or Firm* — Shimon Benjamin; Otterstedt & Kammer PLLC

(57) ABSTRACT

A media stream is delivered to a searcher by identifying a desirable emotional state for the searcher; identifying a current emotional state of the searcher; and estimating a target emotional trajectory that begins with the current emotional state and concludes with the desirable emotional state. Then the target emotional trajectory is matched to an aggregate emotional trajectory of the media stream; the media stream is recommended to the searcher in response to the matching; and a bit stream of the media stream is rendered to the searcher in response to the searcher's acceptance of the recommendation.

20 Claims, 12 Drawing Sheets

(56) References Cited

U.S. PATENT DOCUMENTS

| | | | |
|---|---|---|---|
| 2015/0143392 A1 | 5/2015 | Silveira-Filha et al. | |
| 2015/0181291 A1* | 6/2015 | Wheatley ............... | H04N 21/84 |
| | | | 725/10 |
| 2015/0281783 A1 | 10/2015 | Laksono et al. | |
| 2015/0350730 A1* | 12/2015 | el Kaliouby ........... | A61B 5/165 |
| | | | 725/12 |
| 2016/0188674 A1 | 6/2016 | Han | |
| 2017/0007165 A1 | 1/2017 | Jain et al. | |
| 2017/0231490 A1* | 8/2017 | Toth ....................... | A61B 18/02 |
| | | | 600/558 |
| 2020/0296480 A1* | 9/2020 | Chappell, III .......... | G06F 3/011 |

OTHER PUBLICATIONS

M. Caron, et al., "Deep Clustering for Unsupervised Learning of Visual Features," European Conference on Computer Vision (ECCV) Sep. 2018, pp. 1-29.

Unglesbee, "Who Really Killed Blockbuster?" https://www.retaildive.com/news/who-really-killed-blockbuster/564314/ published Oct. 7, 2019, pp. 1-31.

McDuff, et al., "AFFDEX SDK: A Cross-Platform Real-Time Multi-Face Expression Recognition Toolkit," CHF 16 Extended Abstracts, May 2016, pp. 1-4.

\* cited by examiner

MEDIA STREAM DELIVERY

BACKGROUND

The present invention relates to the electrical, electronic, and computer arts, and more specifically, to delivery of electronic entertainment media streams.

There is a vast array of electronic entertainment media content—far more than any person can sample in the person's entire lifetime. Thus, curation or recommendation of media content has become a key aspect of entertainment delivery. Current recommenders use one or more of the following approaches: social graphing; content based recommendation; or collaborative filtering.

Recommendations based on social graphing look at recommendations made by a user's family or friends, or by people whom the user follows on a social media platform. Social graphing presumes that all people who interact with each other have closely similar tastes. In many cases, however, tastes and emotional responses to media content vary widely among people linked by a social graph.

Content-based recommenders build a user profile for each user. The user profile consists of content the user previously liked, and this is matched up to content descriptors (i.e. keywords) in order to provide similar recommendations. These keywords are quite generic (e.g., user is interested in "historical drama") and hence do not capture nuances of a media content sequence (media stream) that is generically described as "an emotional rollercoaster" or as "light reading."

Collaborative filtering works on the concept of "people who gave similar ratings to the content that you viewed and rated, also liked this content that you haven't seen/rated yet." User profiles are generated for every user based on what content each user has liked/disliked, and then the user profiles are clustered by similarity (i.e. vector clustering). When looking for recommendations, the system looks at the cluster closest to the user, then picks content liked by the cluster that the user hasn't yet seen or reviewed. Efficient clustering requires a complex vector formed by many user recommendations. Often, each user reviews media content using user-specific metrics (which are subjective). The clustering algorithm presumes that all users in a cluster had similar metrics for their ratings of content. The collaborative filtering approach tends to produce "filter bubbles" where only popular content is recommended. It also can produce "off" recommendations when different members of a cluster have highly reviewed the same media for divergent reasons.

SUMMARY

Principles of the invention provide techniques for media stream delivery. In one aspect, an exemplary method for delivering electronic media content includes retrieving from an electronic database a bit stream of a media stream. The method also includes establishing an aggregate emotional trajectory of the media stream by, for each viewer of a plurality of viewers: rendering the bit stream to that viewer via an electronic device; establishing an emotional trajectory of that viewer by continuously measuring that viewer's emotional state, via one or more sensors, throughout that viewer's experience of the rendered bit stream; and aggregating the emotional trajectories of the plurality of viewers to obtain the aggregate emotional trajectory of the media stream. The method also includes determining a target emotional trajectory for a searcher; matching the aggregate emotional trajectory of the media stream to the target emotional trajectory for the searcher; recommending the media stream to the searcher in response to the matching; and rendering the bit stream of the media stream to the searcher in response to the searcher's acceptance of the recommendation.

According to another aspect, an exemplary method for delivering a media stream includes retrieving from an electronic database bit streams of each of a plurality of reference media streams other than the stream to be delivered, in association with aggregate emotional trajectories of each of the plurality of reference media streams. The exemplary method then includes training a neural network classifier to produce aggregate emotional trajectories of the reference media streams in response to bit streams of the reference media streams, using the bit streams and aggregate emotional trajectories of the reference media streams as training input data and training output classifications, respectively; and inferring the aggregate emotional trajectory of the media stream by retrieving from the electronic database a bit stream of the media stream and then providing the bit stream of the media stream as input to the trained neural network classifier. The exemplary method also includes obtaining a target emotional trajectory of a searcher; matching the target emotional trajectory to the aggregate emotional trajectory of the media stream; recommending the media stream to the searcher in response to the matching; and rendering the bit stream of the media stream to the searcher in response to the searcher's acceptance of the recommendation.

According to another aspect, an exemplary method for delivering a media stream includes identifying a desirable emotional state for a searcher; identifying a current emotional state of the searcher; and estimating a target emotional trajectory that begins with the current emotional state and concludes with the desirable emotional state. The method also includes matching the target emotional trajectory to an aggregate emotional trajectory of the media stream; recommending the media stream to the searcher in response to the matching; and rendering a bit stream of the media stream to the searcher in response to the searcher's acceptance of the recommendation.

One or more embodiments of the invention or elements thereof can be implemented in the form of a computer program product including a computer readable storage medium with computer usable program code for facilitating the method steps indicated. Furthermore, one or more embodiments of the invention or elements thereof can be implemented in the form of a system (or apparatus) including a memory that embodies computer executable instructions, and at least one processor that is coupled to the memory and operative by the instructions to facilitate exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

In view of the foregoing, techniques of the present invention can provide substantial beneficial technical effects. For example, one or more embodiments provide one or more of:

Efficient delivery of a media stream that matches the emotional trajectory preferences of a searcher for media content.

Efficient tagging of media content with corresponding emotional trajectories.

Cross domain recommendations of media streams that match a user's preferred emotional trajectory.

Inference of an emotional trajectory for a media stream that has not been reviewed by any user.

Reduced processing power requirements for inferring the emotional trajectory of a media stream that has not been reviewed by any user.

These and other features and advantages of the present invention will become apparent from the following detailed description of illustrative embodiments thereof, which is to be read in connection with the accompanying drawings.

DETAILED DESCRIPTION

When a person rates a movie, the person may say that the person likes the movie. What the person actually means is that the person enjoys the way the movie makes the person feel. When people give a recommendation, they produce a very crude summary of their complex emotional journey. Conventional recommender systems then profile people and group them together based on many crude summaries that miss the nuances of how and why each person responded to a given media content sequence (media stream). By contrast, an aspect of the invention is that a media stream is delivered in response to a potential viewer's acceptance of an invitation or recommendation that is based on matching the "emotional trajectory" of the media stream to a target emotional trajectory for the potential viewer.

Consider, for example, the movies "Cool Runnings" and "Wonder." These movies were produced twenty four years apart (1993 and 2017, respectively) and have completely different subject matter (respectively, the travails of a Jamaican bobsled team and of a New York boy with a facial deformity). Respective summaries of the movies would not show much similarity. However, the movies are closely similar in their emotional trajectories: both move from embarrassed→pessimistic→hopeful disappointed proud.

Figure 1:
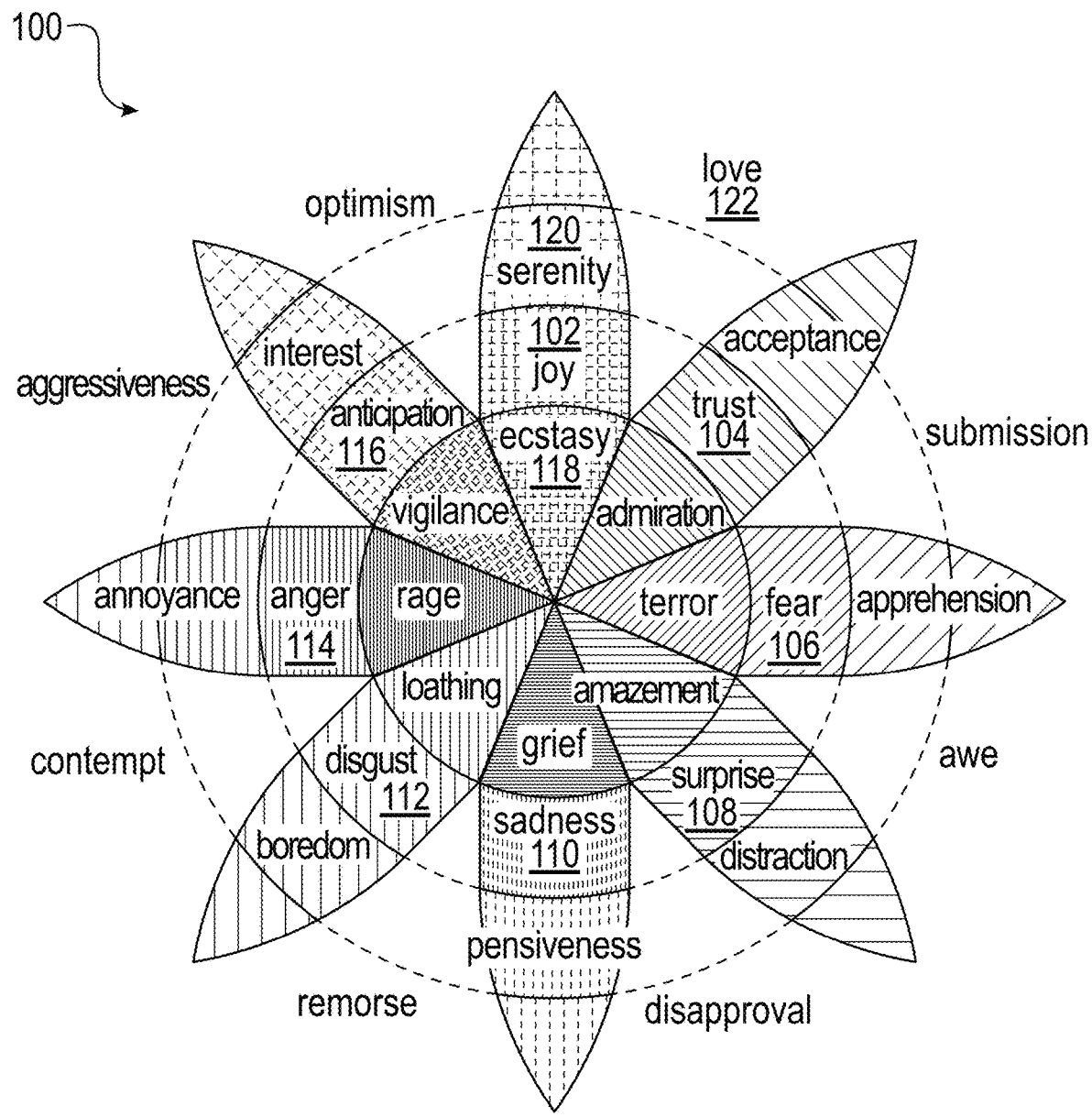
FIG. 1 depicts a Plutchik emotion wheel diagram.

In this context, an "emotional trajectory" is a sequence of emotional states that are expressed by the media stream and/or experienced by the potential viewer. In 1980 Robert Plutchik constructed a wheel-like diagram 100 of emotions, shown at FIG. 1. FIG. 1 depicts eight basic emotions, plus eight derivative emotions each including two basic ones. The basic emotions are: joy 102, trust 104, fear 106, surprise 108, sadness 110, disgust 112, anger 114, and anticipation 116. Closer to the center represents higher intensity of the same class of emotion. For example, consider the petal of the diagram 100 with joy 102 as the basic emotion. Moving towards the center shows ecstasy 118 as the more intense form of joy, and moving away from the center show serenity 120 as the less intense form of joy. Derivative emotions are composed of two basic emotions, for example love 122 is a combination of the basic emotions of joy 102 and trust 104.

Figure 2:
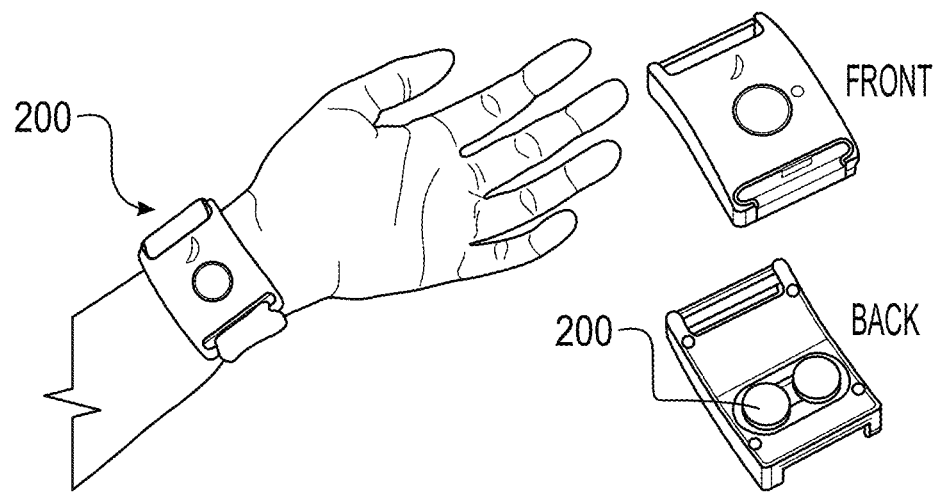
FIG. 2 depicts a biometric sensor for detecting emotional responses.
Figure 3:
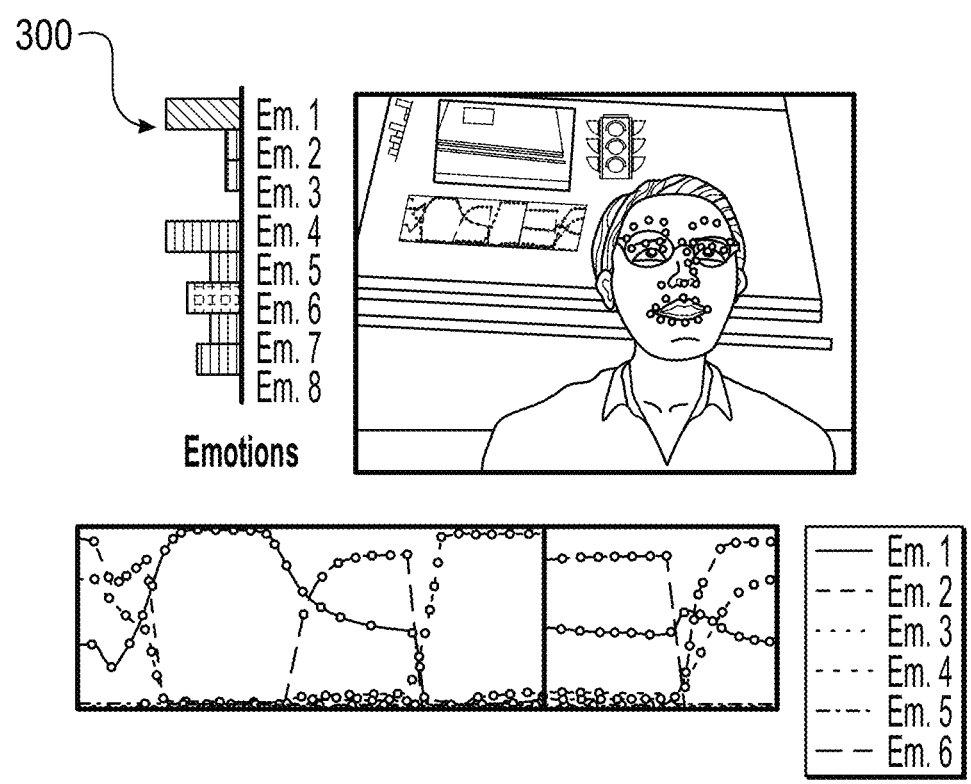
FIG. 3 depicts a screenshot of software for assessing emotional responses based on recognition of facial expressions, according to an exemplary embodiment.

Techniques to measure emotion, based on physiologic signaling or facial expressions, are known. For example, FIG. 2 depicts a wearable, wireless biosensor that measures emotional arousal via skin conductance (aka galvanic skin response). This is a form of electrodermal activity that grows higher during states such as excitement, attention or anxiety and lower during states such as boredom or relaxation. The sensor includes electrical contacts 202, as well as a thermometer that measures temperature and an accelerometer that measures physical activity. As another example, FIG. 3 depicts a facial expression of a user using a combination of one or more machine learning models (e.g., pretrained facial recognition and expression detection models, neural network model trained to infer emotion from physiologic signals, etc.) that detect anatomical facial muscle movements ("action units") and characterize action unit sequences or combinations to estimate the emotional state of a person being monitored by the one or more machine learning models. For example, an implementation of such models using "smart glasses" can recognize six facial expressions: thinking, agreeing, concentrating, interested, confused, and disagreement. Given the teachings herein, the skilled artisan will appreciate that other products and techniques may be equally effective for purposes of embodiments of this invention; although such technologies have not been previously employed in a method for media content delivery based on emotional trajectories, as disclosed herein.

Figure 4:
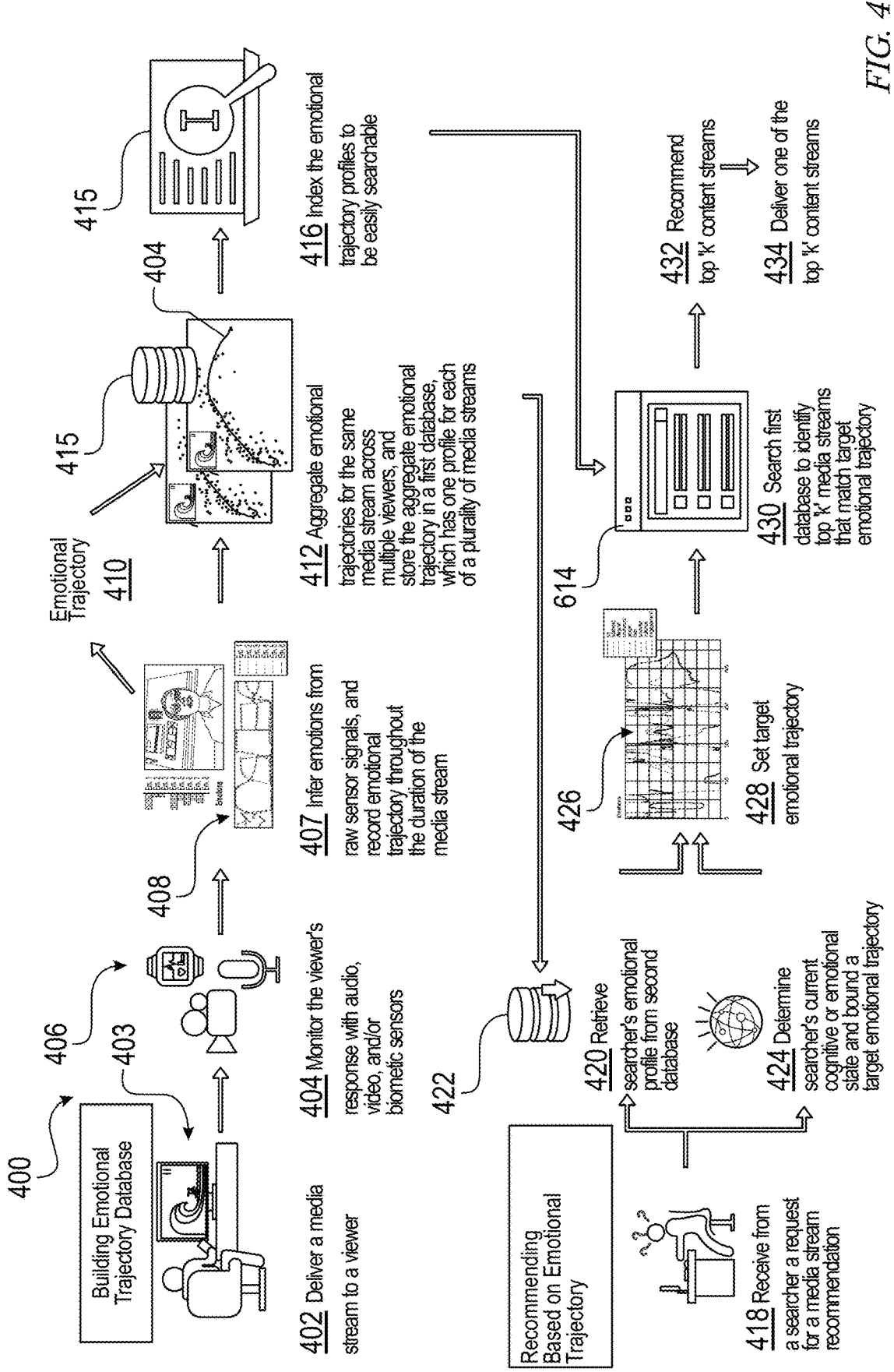
FIG. 4 depicts, in a schematic, general principles of a method for media stream delivery based on emotional trajectories, according to an exemplary embodiment.

FIG. 4 depicts, in a schematic, general principles of an exemplary method 400 for media stream delivery based on emotional trajectories, according to an exemplary embodiment.

At 402, a media stream 403 (e.g., a movie, a book, a website, or music) is delivered to a viewer. Note that although "viewer" is used in describing this exemplary embodiment, "listener" might also be an accurate word in certain other embodiments. Note, also, that in one or more embodiments, delivering a media stream involves retrieving from an electronic database a bit stream of the media stream, and rendering the bit stream to a viewer via an electronic device. Exemplary electronic devices include video displays, audio speakers, and/or haptic devices.

At 404, an apparatus implementing the exemplary method monitors the viewer's response with audio, video, and/or biometric/physiologic sensors 406. At 407, the apparatus infers emotions from raw sensor signals 408, and records the viewer's emotional trajectory 410 throughout the duration of the media stream 403, i.e. throughout the viewer's experience of the media stream. The apparatus records the emotional trajectory 410 as a sequence of intensities of the eight basic emotions, as illustrated in the graph of the emotional trajectory 410 in FIG. 5. Signals used to infer emotion may include physiological signals such as heart rate, ECG, skin conductance, body temperature, among others. The system may also use a video camera to monitor the facial expressions, body language, posture, and movement of the viewer in order to infer emotion. Finally, a microphone may be used to monitor the audio from the viewer; in one or more embodiments the microphone filters out any audio from the media that the viewer is consuming.

Generally, a viewer's emotions can be inferred from the various raw sensor signals 408 by inputting the signals to a previously trained neural network (e.g., as used in the Affdex software), in a manner that will be apparent to the skilled worker. For example, in one or more embodiments, a neural network can be trained to infer emotion from sensor signals on a presumption of viewer empathy. Such training uses emotions inferred from the content of one or more media streams (e.g., by natural language processing (NLP) of the media stream(s) text) as the training output(s) for the neural network, supplying as the training input(s) the raw sensor signals from viewer(s) consuming the one or more media stream(s). The empathy presumption is that the viewer's emotions will match the contemporaneous emotions inferred from the media stream content by NLP. As another example, a neural network can be trained to infer emotion from physiologic signals or facial expressions based on monitoring the signals and/or expressions of test subjects who contemporaneously indicate how they are feeling using, e.g., a computer-based questionnaire. An exemplary training process is discussed with reference to FIG. 13, below.

At 412, the apparatus aggregates emotional trajectories for the same media stream across multiple viewers, and stores the aggregate emotional trajectory 414 in a first database 415, which has one profile for each of a plurality of media streams. At 416, the apparatus indexes the emotional trajectory profiles to be easily searchable. Step 416 is discussed in more detail with reference to an indexing module 606, operation of which is shown in a flowchart at FIG. 10.

At 418, the apparatus receives from a searcher a request for a media stream recommendation. There are two options for how to proceed after receiving the request.

At 420, the apparatus tries to retrieve the searcher's emotional profile from a second database 422. The searcher's emotional profile may include, for example, an aggregate of the searcher's emotional trajectories in response to various media streams that the searcher has given high review ratings.

At 424, the apparatus determines the searcher's current cognitive or emotional state, and bounds a target emotional trajectory 426. For example, if the apparatus detects that the searcher is feeling "fragile," then the target emotional trajectory should probably not contain significant swings of emotion or from a remedial point of view the trajectory could include reassuring emotions such as "trust" and "acceptance."

At 428, the apparatus sets the target emotional trajectory 426. For example, the target emotional trajectory might lead from the searcher's current emotional state to a desirable emotional state, e.g., from sad to happy or from stressed to relaxed or from relaxed through frightened to relieved. Alternatively, the target emotional trajectory might match the searcher's emotional profile. As another alternative (not shown), the target emotional trajectory could match the searcher's selections from at least one menu of desired emotional experiences.

At 430, the apparatus searches the first database 415 to identify a list 614 of a top 'k' number of media streams (media content sequences) that match the target emotional trajectory 426.

In one or more embodiments, "matching" emotional trajectories is accomplished using a vector algorithm that seeks minimum distance on the Plutchik emotion wheel from each point of the target emotional trajectory to each corresponding point of one or more emotional trajectories retrieved from the first database 415, where the points correspond to intensities of the dominant emotion at any given time. For example, if the target emotional trajectory is relaxed through frightened to relieved, then a suitable vector algorithm would return a moderate probability match for a first retrieved emotional trajectory that had the sequence serenity to surprise to joy, but would return a low probability match for a second retrieved emotional trajectory that had the sequence sadness to anger to acceptance.

Figure 5:
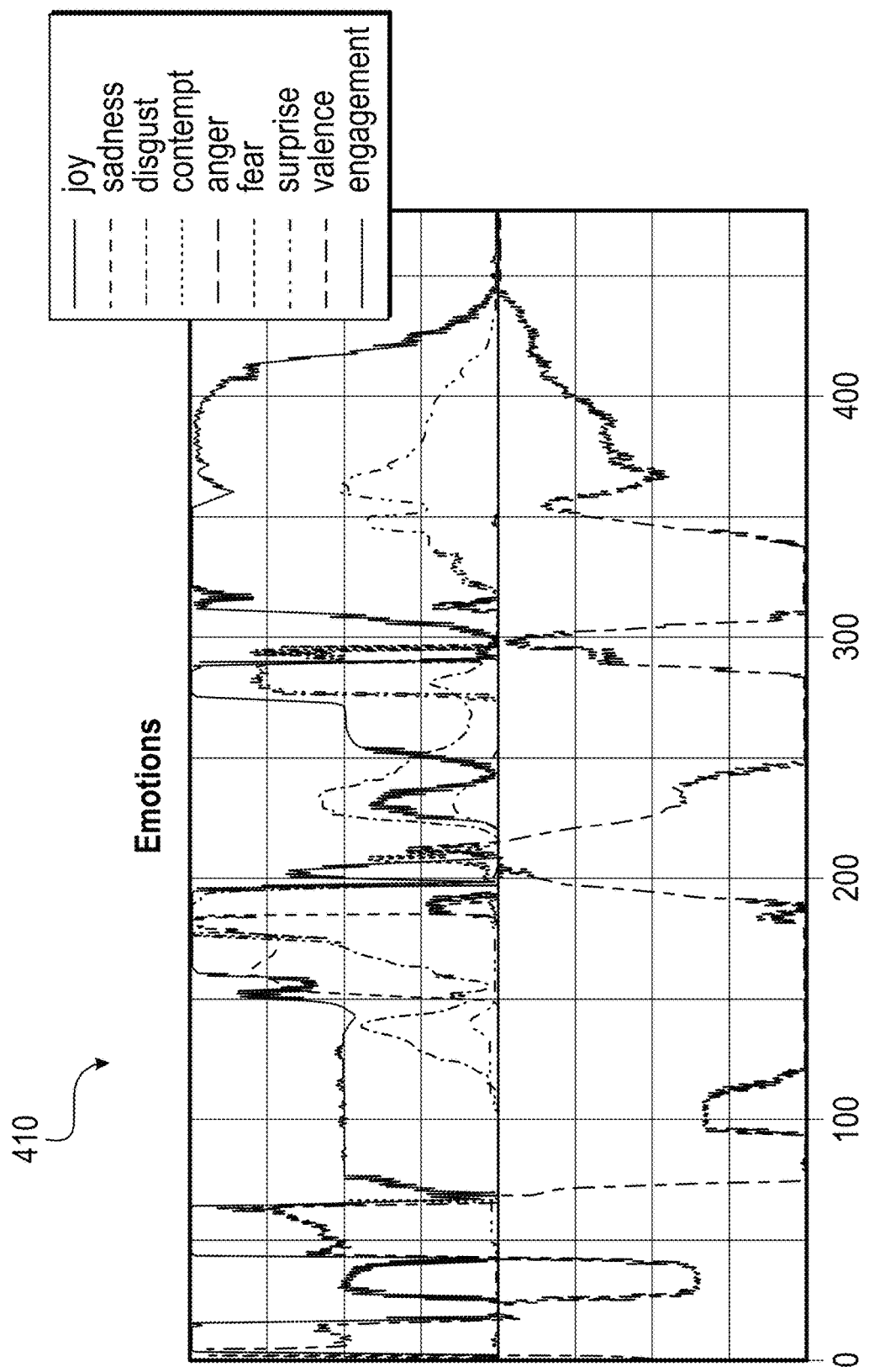
FIG. 5 depicts a graph of an emotional trajectory.

In one or more other embodiments, "matching" the emotional trajectory is given by the intensity of the basic emotions at each point in time (joy, sadness, disgust, contempt, anger, fear, surprise, engagement). Note that these signals in FIG. 5 are continuous, not discrete. The emotion at any point in time is given by the combination of these intensities of these basic emotions at the specific time. The overall emotional trajectory is given by all of the signals together, as a function of time. Under such embodiments, the "matching" algorithm would compute the similarity between the target emotional trajectories (e.g., represented as vector A) and the emotional trajectories (e.g., represented as vector B) stored in the database, using continuous-time multi-dimensional signals (corresponding to the continuous measurement of each of the basic emotions). In one exemplary embodiment, the matching algorithm is the cosine similarity algorithm that measures the cosine of the angle between the two vectors projected in a multi-dimensional space. Note that the value of each emotional trajectory needs to be converted to numerical value. Thus, the similarity (i.e., matching) between A and B can be calculated as:

$$\text{similarity}(A, B) = \frac{A \cdot B}{\|A\| \times \|B\|} = \frac{\sum_{i=1}^{n} A_i \times B_i}{\sqrt{\sum_{i=1}^{n} A_i^2} \times \sqrt{\sum_{i=1}^{n} B_i^2}}$$

Other methods for assessing similarities of emotional trajectories include Pearson's correlation or cosine similarity:

$$sim_{cos}(u, v) = 1 - \frac{(u - \bar{u}) \cdot (v - \bar{v})}{\|u\|\|v\|}$$

or mean squared difference:

$$msd(u, v) = \frac{1}{|I_{uv}|} \sum_{i \in I_{uv}} (r_{ui} - r_{vi})^2.$$

Returning now to FIG. 4, at 432, the apparatus recommends to the searcher the top 'k' media streams. At 434, in response to an acceptance 435 (not shown in FIG. 4; seen in FIG. 6 discussed below) that is received from the searcher, the apparatus delivers to the searcher one of the top 'k' media streams from a third database 436 (not shown in FIG. 4; seen in FIG. 6 discussed below). As mentioned, delivery includes, for example, retrieving and rendering a bit stream of the media stream via one or more electronic devices.

Figure 6:
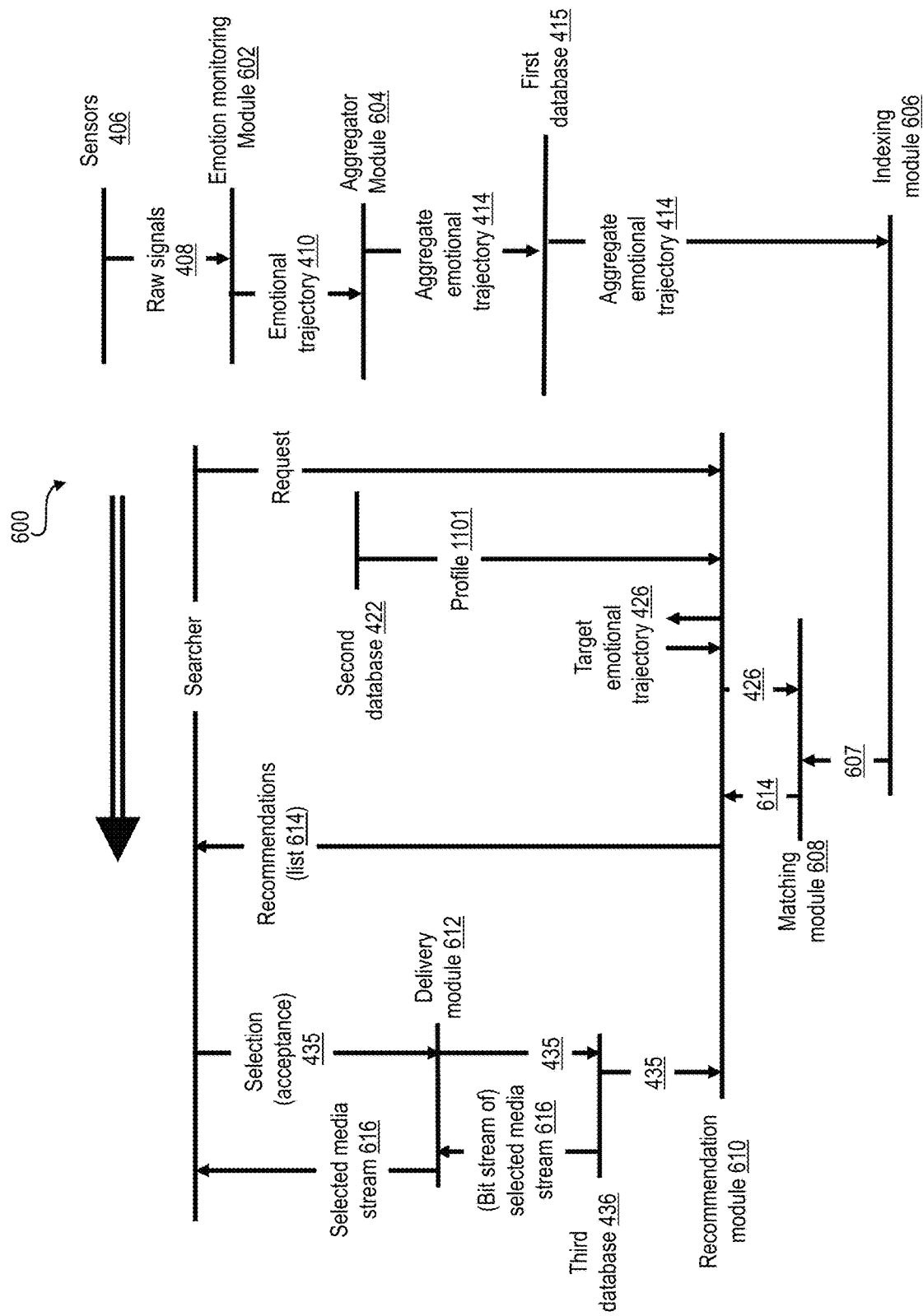
FIG. 6 depicts in a schematic data flows among modules of an apparatus for implementing the method for media stream delivery, according to an exemplary embodiment.
Figure 10:
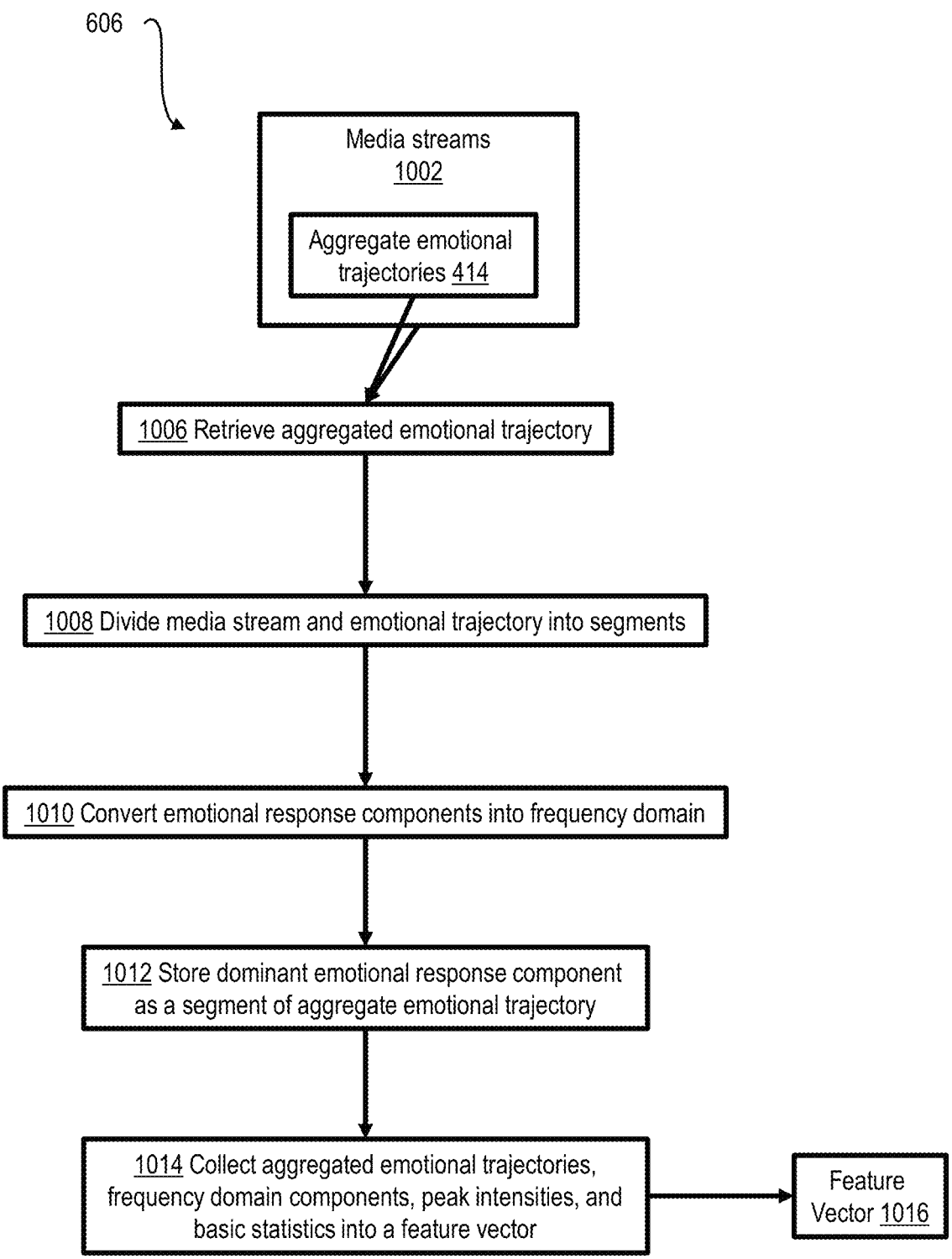
FIG. 10 depicts in a flowchart operation of an indexing module of the apparatus of FIG. 6, according to an exemplary embodiment.

FIG. 6 depicts in a schematic data flows among modules of the apparatus 600 that implements the method of FIG. 4. The modules include the sensor(s) 406, the first database 415, the second database 422, the third database 436, an emotion monitoring module 602 that continuously measures emotion while consuming media, an aggregator module 604 that aggregates emotional trajectories for a media stream across multiple viewers, an indexing module 606 that indexes the media streams based on the aggregated emotional trajectories, a matching module 608 that measures similarities between media streams based on the emotional trajectory profile, a recommendation module 610 that recommends new media streams to a searcher based on the target emotional trajectory 426, and a content delivery module 612 that delivers a media stream to the searcher in response to the searcher's acceptance of a recommendation produced by the recommendation module 610. The sensors 406 pass to the emotion monitoring module 602 the raw signals 408 from a given viewer and media stream. The emotion monitoring module 602 then establishes the emotional trajectory 410 and passes that to the aggregator module 604. The aggregator module 604 stores the aggregate emotional trajectory 414 in the first database 415. The indexing module 606 arranges the first database 415 to sort media streams according to their respective aggregate emotional trajectories 414. FIG. 10 further describes one such implementation of generating the aggregate emotional trajectory and the encoding thereof into an indexing feature vector. The matching module 608 uses the indexing module 606 to retrieve from the database 415 a plurality of indices 607 associated with the aggregated emotional trajectories 414 that correspond to a plurality of media streams and that are matched to the target emotional trajectory 426. To this end, the target emotional trajectory 426 is indexed by module 606 and compared to other indices 607 for similarity matching. In response to a searcher's request, the recommendation module 610 retrieves the searcher's profile 1101 from the second database 422, produces the target emotional trajectory 426, and uses the matching module 608 to obtain an indexed list 614 of the top 'k' media streams that match the target emotional trajectory 426, along with their associated emotional trajectories. The delivery module 612 receives the searcher's selection (acceptance) of one of the recommended media streams and then, in response to the searcher's acceptance 435, retrieves a selected media stream 616 from the third database 436 and delivers the selected media stream to the searcher. The accepted selection, along with unaccepted selections, are returned to the recommendation module for updates and learning of the correct matching associated with the profile 1101.

In the emotion monitoring module 602, each emotional trajectory 410 is recorded against time, based on signals 408 received from the sensor(s) 406. In one or more embodiments, it is pertinent to estimate which moment in time corresponds to which point in a viewer's experience of the media stream 403. Movie content, for example, is the most straightforward as the apparatus knows which moment of the movie is being played. By contrast, for asynchronous media such as a book, it may be useful to detect when the viewer is reading the book and when the viewer is away from the book. Given that book reading generally happens in multiple sessions, one or more embodiments provide techniques to start, pause, resume, and end a book reading session. In one or more embodiments, all of the sensors that read the emotional trajectory data will feed into a smartphone application (or application on an e-book reader device) that has the ability to start, pause, resume, and end reading sessions. A user then can use the application to assign a portion of the emotional trajectory 410 to a particular segment (reading session) of a book being read. For e-books it is easier to ascertain which page of the book is being viewed concurrently with the viewer's emotional response.

For more advanced tagging purposes, i.e. linking emotional responses to particular stimuli within the media stream, consideration may have to be made for lingering/delayed emotions, which is an issue for trying to infer which part of the content is responsible for the emotion. However, it is not as much an issue for the task of aggregating emotional trajectories. For example, note that a strict correlation of an emotional response to a moment of a media stream is typically far less important than is the overall emotional trajectory experienced in response to the media stream as a whole.

Figure 7:
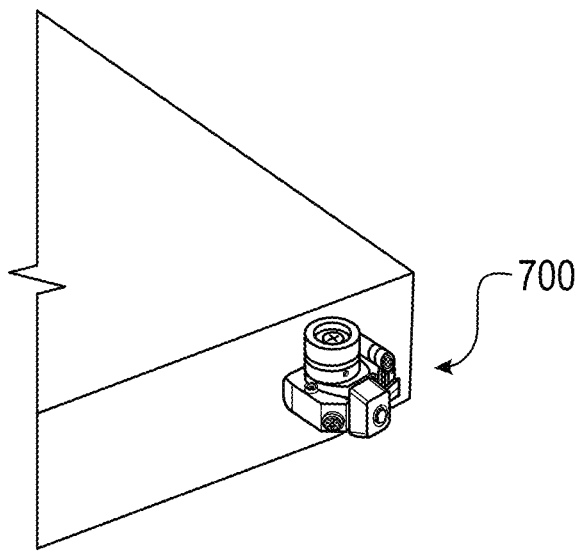
FIG. 7 depicts an exemplary camera sensor used by an emotion monitoring module of FIG. 6.

Useful sensors 406 may include any one or a combination of the following:

A camera 700, of which an example is depicted in FIG. 7, may be attached (or built in) to an (audio)visual display device (e.g., tablet, laptop computer, cellular phone, or e-book reader), or may attached to a physical bookmark inserted into a paper book. The camera 700, in cooperation with software such as (by way of non-limiting example) Affectiva's Affdex software, can extract a viewer's emotional trajectory by measuring the viewer's facial expressions. The system does not need to store the photos or video, but rather just the extracted emotion.

Figure 8:
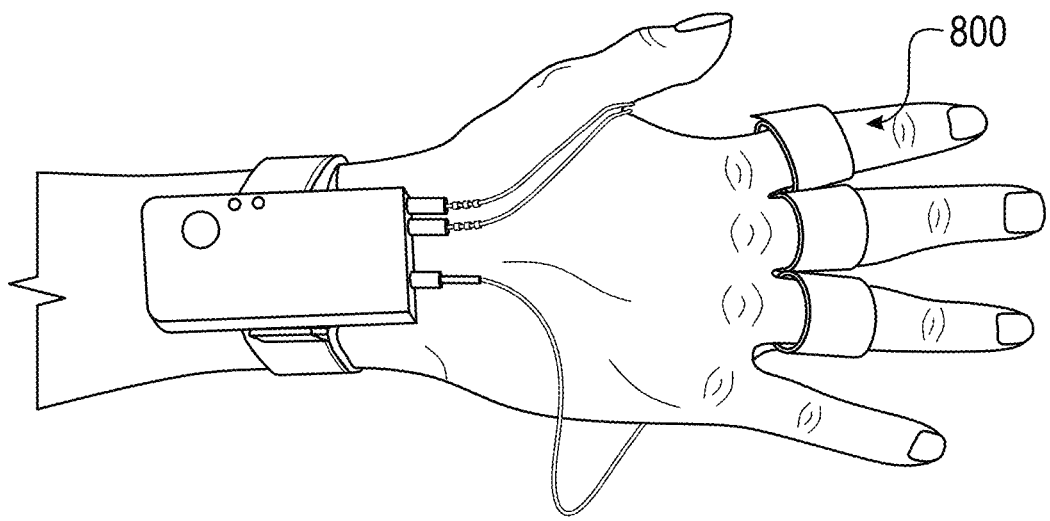
FIG. 8 depicts an exemplary galvanic skin response sensor used by the emotion monitoring module of FIG. 6.

Galvanic skin response (GSR) sensors, an example of which is depicted in FIG. 8, may be in the form of pads on the back of a reader device or in the form of strap-on sensors 800 for the hands, which will measure the change in sweat gland activity on the user's hands. Sweat gland activity correlates with a user's "emotional arousal" or "valence,"

which (with reference to FIG. 1) is an indication of how close the user is to the central peak of the Plutchik emotion wheel 100.

A sensor that measures how quickly the reader turns pages: On a reader device, this can be measured directly from button presses, and on a physical book this could take the form of accelerometer (and/or tilt) sensors embedded into a physical bookmark. Faster page turning can imply emotional arousal, but if the page turning is too fast, or in bunches of pages, it can signal boredom (skipping content). Slow turning of the pages can indicate interest (lots of detail or complexity, perhaps re-reading of passages).

Audio recording in the form of a microphone on the reader or embedded into a bookmark: It is possible to detect laughter from audio cues (laugh-out-loud moments).

Heart-rate monitor, in the form of a fitness band or smart watch. This, optionally in combination with natural language processing of contemporaneous media content, can detect frightening moments or moments of high tension or emotional valence.

Posture detection can be implemented, for example, using the afore-mentioned video analysis from the camera 700, or by using accelerometers and a gyroscope, either from the user's smartphone, or from a smart watch or fitness band. The posture can provide an indication of boredom or excitement as users shift their postures based on the amount of attention they are paying.

Figure 9:
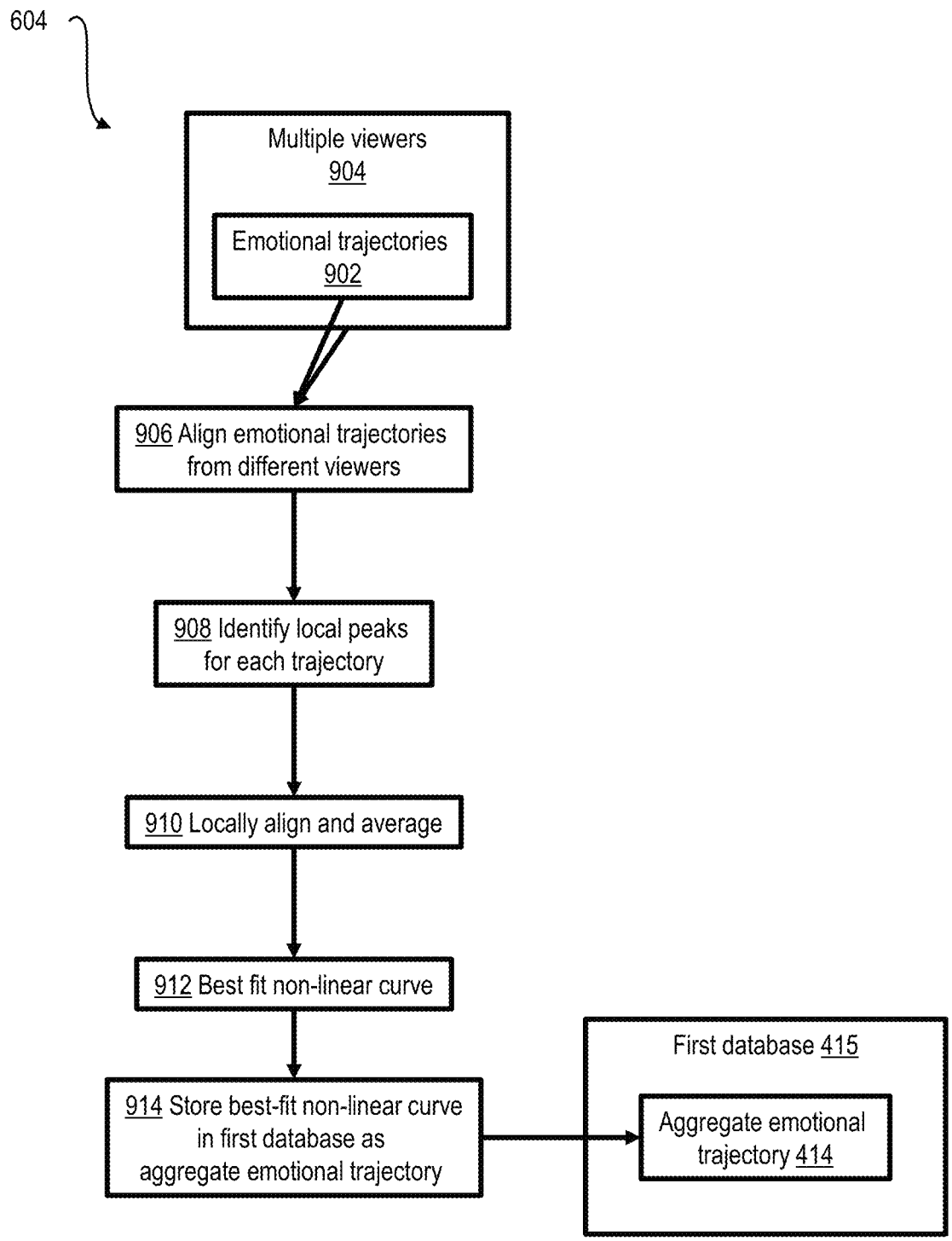
FIG. 9 depicts in a flowchart operation of an aggregating module of the apparatus of FIG. 6, according to an exemplary embodiment.

FIG. 9 depicts a flowchart of operation of the aggregating module 604, which aggregates emotional trajectories 902 across multiple viewers 904. Aggregation at 906 aligns emotional trajectories from different viewers, which are attached to a single media stream, by identifying at 908 local peaks for each trajectory (using known peak-finding algorithms). Local peaks that are within a pre-determined window of each other are then, at 910, further locally aligned and averaged. This allows a general trend for emotional trajectory to be extracted while cancelling out individual idiosyncratic differences (e.g., different reaction times to emotional stimuli).

Emotional responses once collated can be aggregated by using an attention-based machine learning algorithm or ensemble methods at 912 to best fit a non-linear curve to the emotional responses for the viewing session. At 914, the best fit curve is stored in the first database 415 as the aggregate emotional trajectory 414.

FIG. 10 depicts in a flowchart operation of the indexing module 606 for indexing the media streams 1002 according to their respective aggregate emotional trajectories 414. This operation allows for the entire emotional trajectory or subsets within predetermined media stream windows (e.g., time-stamped beginning and ending scenes in a movie) to be encoded by a feature vector. The feature vectors thus provide a summary of the aggregated emotional responses as a function of the streaming window and are thereafter compared for similarities by the matching module 608, storing the expected aggregate emotional response to the streaming window in the first database 415. The feature vectors may additionally provide a unique key to efficiently retrieve the entire aggregated emotional response from the first database 415.

The indexing module 606 provides a hierarchical method of extracting and storing dominant emotional responses in order to efficiently index the emotional trajectory of the media. The indexing module 606, at 1006, retrieves an aggregated emotional trajectory related to the relevant time-stamped media stream. At 1008, the indexing module 606 divides the media stream, and consequent emotional response curves are divided into different segments (e.g., different scenes in a movie), offering a high-level representation along with the emotional progression of the media stream at distinct intervals.

At 1010, the different emotional response components are converted into the frequency domain, identifying the key or dominant component pertaining to each emotional response. Then, at 1012, the dominant emotional response component for each segment is stored as a segment of the aggregated emotional trajectory along with peak emotional intensities and basic statistics (average, variance, range). By way of example, the peak intensities are defined by values associated with the eight basic emotions identified by Robert Plutchik, with intensity values that are calculated by an emotional recognition system like the biosensor or facial recognition models previously discussed and that are further defined as the probabilities of detecting those specific emotions or the normalized intensities thereof. For example, for five scenes in a movie, the trajectory is stored as: (joy, 0.2), (sad, 0.15), (hopeful, 0.5), (surprise, 0.75), (joy, 0.3).

Finally, at 1014, the aggregated emotional trajectories, the frequency domain components, the peak intensities and the basic statistics are collected into a well-defined feature vector 1016 associated with the media stream.

The matching module 608 measures similarities between media streams based on their aggregate emotional trajectories 414 and feature vectors 1016. As the database of (updateable) feature vectors associated with media streams grows, it becomes possible to find similarities between media streams via their feature vectors. In an unsupervised form this process is known as clustering. In one or more embodiments, clustering methods are employed such as agglomerative hierarchical clustering or Deep CNN clustering. One step in clustering is to define a similarity metric. Standard similarity metrics can be used such as Euclidean or Cosine Distance. More advanced, and implementable in one or more embodiments (using, e.g., tags), is to learn multiple (named) metrics from given cases of similarities along named "dimensions" of similarities. By clustering media streams based on their aggregated emotional trajectories, it becomes possible to make quick recommendations in response to a searcher request and to target emotional trajectory.

Figure 11:
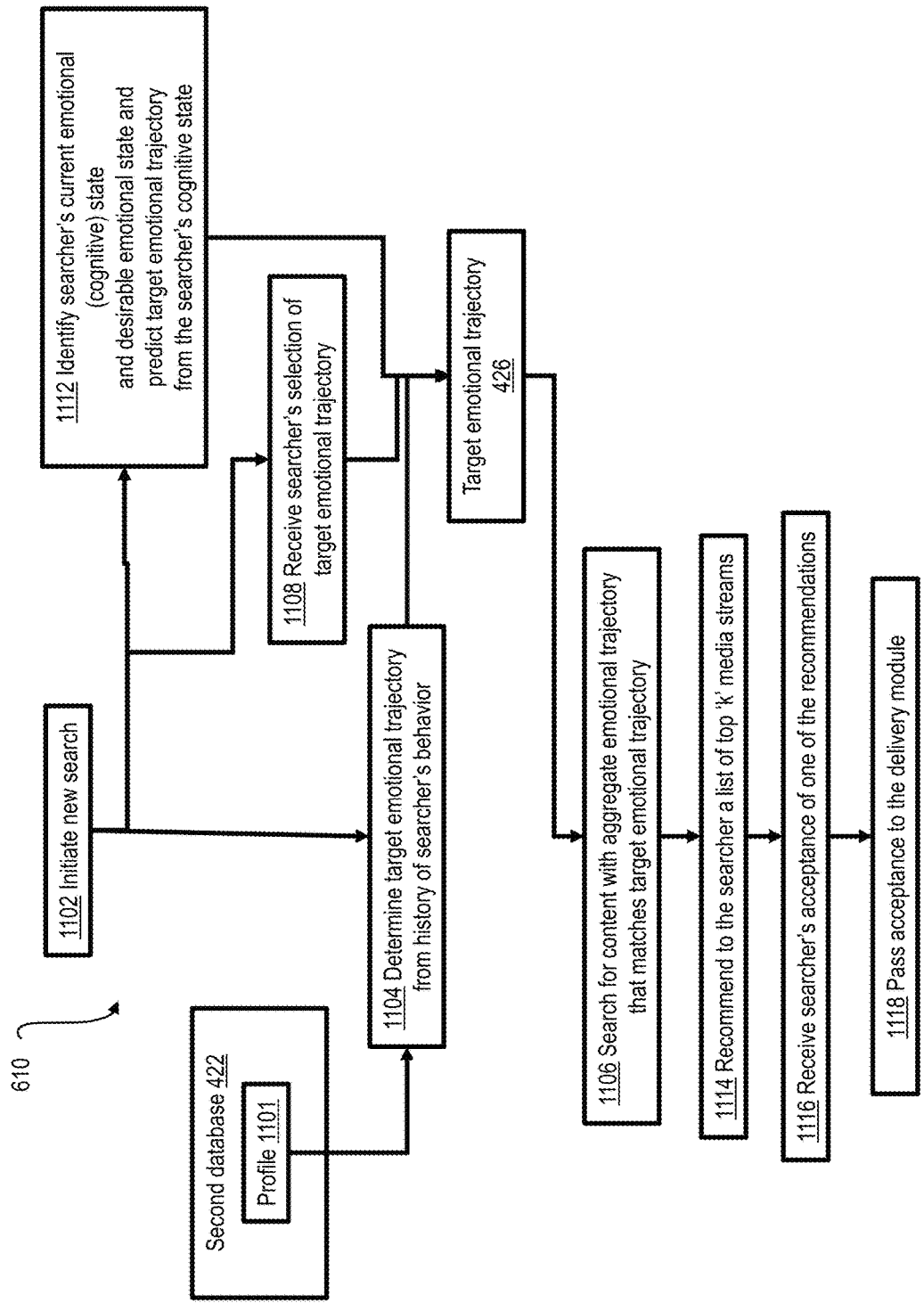
FIG. 11 depicts in a flowchart operation of a recommendation module of the apparatus of FIG. 6, according to an exemplary embodiment.

FIG. 11 depicts in a flowchart operation of the recommendation module 610 for recommending new media streams to a searcher in response to the searcher's target emotional trajectory 426, which may be based on historical preferences, prediction/prescription from a current emotional state, or explicit selections by the searcher. "Searcher" refers to a user who is seeking new media content to view. The searcher may already have a profile 1101 in an emotional trajectory database (second database 422). The profile 1101 comprises all the content that the searcher has historically consumed, along with the searcher's emotional trajectories in response to that content. The database 422 may further record a satisfaction index (e.g., a review rating produced by the searcher) in association with each emotional trajectory. Upon initiating a new search at 1102, at 1104, the recommendation module 610 determines the current emotional response as a prior, along with the target emotional trajectory 426 from the historical behavior of the searcher. At 1106 the system will proceed to search for content with an aggregate emotional trajectory that is similar to the target emotional trajectory.

Alternatively, at 1108 the searcher may input explicitly the desired emotional trajectory profile (e.g. embarrassed→pessimistic→hopeful→disappointed→proud), or perhaps specify a higher level tag such as "emotional rollercoaster" or "tear-jerker". The system at 1106 will then search and recommend content with appropriately matching emotional trajectories.

Alternatively to using the historical preference of the searcher or manual input by the searcher, the system at 1112 may attempt to predict the target emotional trajectory 426 from the searcher's prior, the current cognitive state. Cognitive state (emotional state) may be measured, for example, as discussed above with reference to FIGS. 1-3. For example, if the cognitive state of the searcher is sad, then the system may recommend a target trajectory that goes from sad to happy at the end. As another example, if the user is feeling curious, the system may recommend a target emotional trajectory that leaves the searcher feeling the searcher learned something new. As another example, if the user is feeling stressed, the system may recommend content that is calm and tranquil, which may help alleviate the user's stress. Then at 1106 the system will search for content that matches the target emotional trajectory.

At 1114, the recommendation module 610 recommends to the searcher a list of top 'k' media streams that have aggregate emotional trajectories matched to the searcher's target emotional trajectory. At 1116, receive the searcher's acceptance of one of the recommendations. At 1118, pass the selection to the delivery module 612, inclusive of the accepted recommendation to be streamed 616. Additional unaccepted recommendations along with the cognitive state may be passed to the recommendation module 610 for model retraining.

Figure 12:
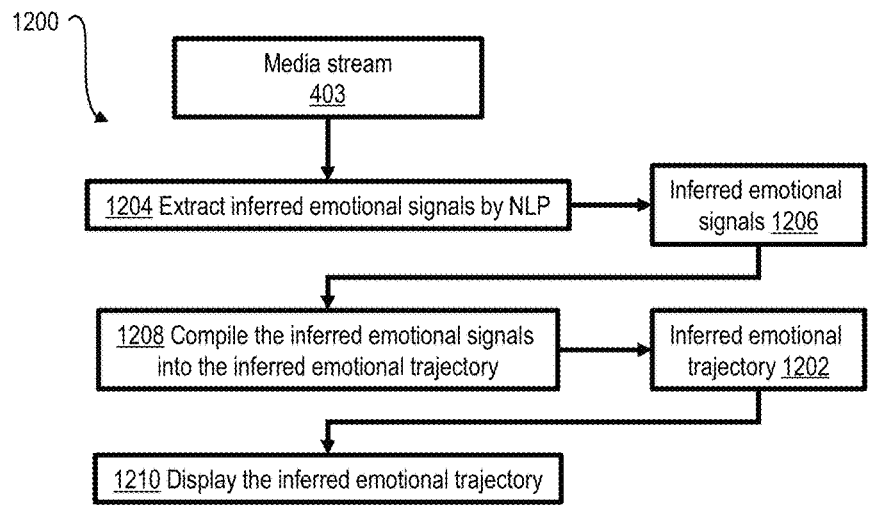
FIG. 12 depicts in a flowchart a method for inferring an emotional trajectory of a media stream, according to an exemplary embodiment.

Referring to FIG. 12, one or more embodiments of the invention incorporate a method 1200 that develops an inferred emotional trajectory 1202 from a media stream 403. At 1204, extract inferred emotional signals 1206 from the media stream 403 by employing natural language processing. The extracting is accomplished by automatically detecting the emotional signals 1206 from texts, images or audio/video of the media stream 403 using natural language processing, voice tone analysis, and/or facial/postural video recognition technology on the media stream. At 1208, compile the inferred emotional signals 1206 into the inferred emotional trajectory 1202. The method 1200 presumes that the emotional signals 1206 that are inferred from the media stream match emotions that would be experienced by a person viewing the media stream. In some instances, however, this may not be true. For example, a media stream in which a character exhibits surprise followed by anger may induce an amused or satisfied emotional response in a viewer, depending whether the character is a comic lead or foil or a villain. Concurrent with extracting the emotional signals, the method 1200 automatically silences the media stream (in cases where the method runs the media stream in real-time, i.e. at normal speed). The method 1200 also can include, at 1210, automatically displaying the inferred emotional trajectory to a viewer or cohort of viewers on a digital cover of the media stream for books, graphical display for video media stream, spoken cue for music content, etc. This display is thereby presented to the user in an easy to consume GUI during the request process of 600, to assist the formulation of a target emotional trajectory.

Figure 13:
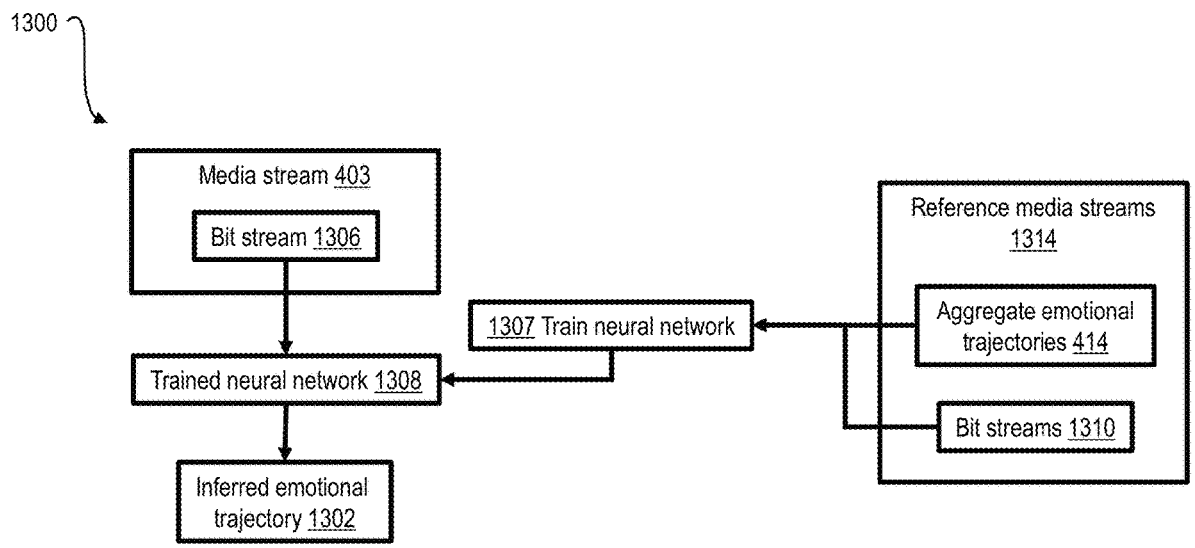
FIG. 13 depicts in a flowchart another method for inferring an emotional trajectory of a media stream, according to an exemplary embodiment.

FIG. 13 depicts in a flowchart another method 1300 for inferring an emotional trajectory 1302 for a selected media stream 403, based on providing a bit stream 1306 of the selected media stream 403 as input to a trained neural network 1308.

Generally, a neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. A neural network can implement supervised, unsupervised, or semi-supervised machine learning.

The neural network 1308 can be trained at 1307, for example, in a supervised fashion, by using the bit streams 1310, aggregate emotional trajectories 414, and indices 607 (see FIG. 6) of a plurality of reference media streams 1314 as training input data and training output classifications, respectively. Thus, in case there are a first plurality of media streams that have a first emotional trajectory (e.g., happy→surprised→confused→angry→sad→hopeful→expectant→vigilant→happy), and a second plurality of media streams that have a second emotional trajectory (e.g., sad→confused→hopeful→happy), then the neural network 1308 is trained at 1307 using the respective bit streams 1310 of those media streams as input data and using the respective emotional trajectories 414 as output data. In one or more embodiments, a recurrent neural network may be particularly suitable for this purpose.

The bit stream 1306 of the selected media stream 403 then is provided to the neural network 1308 as input data, and the output of the neural network 1308 is taken as the inferred emotional trajectory 1302. Advantageously, in one or more embodiments using an adequately trained neural network 1308, the method 1300 reduces processing power requirements for new media streams compared to the method 1200.

Figure 14:
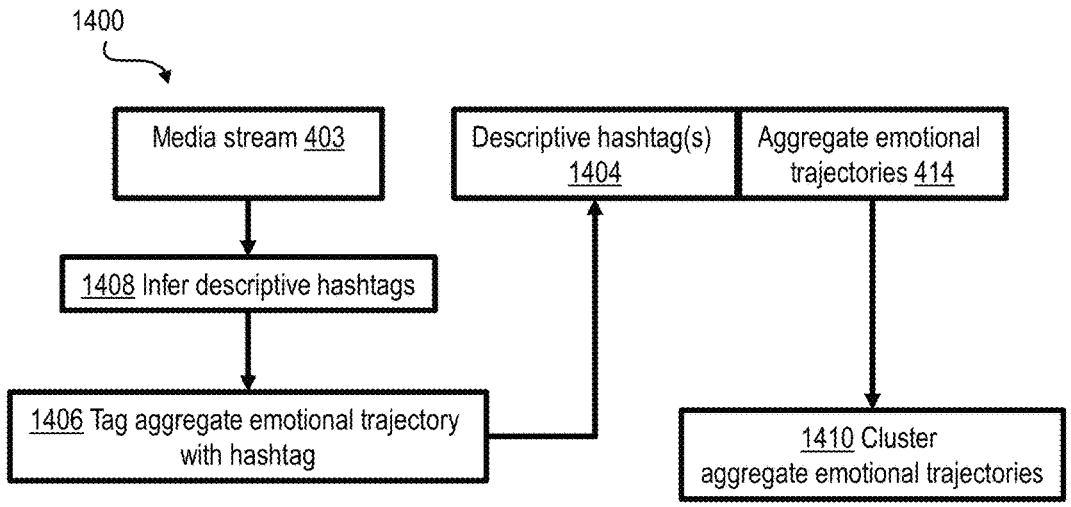
FIG. 14 depicts in a flowchart a method for tagging emotional trajectories with high level descriptors, according to an exemplary embodiment.

In one or more embodiments, as shown in FIG. 14, a method 1400 is implemented for tagging aggregate emotional trajectories 414 with high-level descriptors 1404. Using high-level natural language processing (NLP), at 1406 tag an aggregate emotional trajectory 414 with one or more descriptive hashtags 1404 that are inferred at 1408 from the associated media stream 403. For example, if a movie 403 is inferred to be a romance movie based on natural language processing (NLP) of its dialogue, then at 1406 the emotional trajectory 414 for the movie 403 may be tagged #romance. Additionally, at 1410 cluster similar emotional trajectories and then look for commonalities amongst the underlying media streams that would aid tagging. For example, both "Cool Runnings" and "Wonder" may have within their blurb descriptions the phrase "feel good," then tagging the same emotional trajectory as #feelgood would therefore have a higher ranking than a tag inferred from one media source only. As another example, when a collection of media streams are tagged "funny," the matching module 608 then can look for similarities amongst the emotional trajectories of the collection. A discovered feature vector "mask" or metric then can be stored as the metric that focuses on the funny aspects of media content. This then can be used to measure the degree of humor between media streams. Not only does this allow other generically funny media streams to be found, but also other streams that are specifically funny in ways that are similar to a given stream. The metrics can be learned using machine learning model (e.g., a variant of attention-based neural tag recommendation) based on historical tags. Alternatively, this method of metric discovery can be implemented using a trained machine learning model such as deep neural network model. In one or more embodiments, principal component analysis (PCA) can be used. PCA is a linear algorithm for extracting the main directions along which points vary. This can be used to maximize distinguishability, along a few reduced dimensions, between known clusters and therefore be used to place new data points into these clusters. In other embodiments, an auto-encoder can be used. Auto-encoders are a neural network architecture for dimensionality reduction and synthetic generation, capturing in a non-linear way how points vary. The dimensionality reduction part may be used to produce a reduced vector for clustering points. The clustering may be used to place new data points into known clusters.

At search time, the searcher may also provide tags such as "#feelgood" and the media streams with the associated emotional trajectory may be presented. Via the tags, the system can also help learn a mapping between emotional trajectories associated with different media types. For example, consider the emotional trajectory of a 120 minute movie, versus the emotional trajectory of a 40 minute TV show. It may be difficult for the system to map between these two media streams based on the difference in duration of emotional trajectory. However, if both of these media streams are tagged as "uplifting", then the system can learn the mapping, thereby adding content searching.

Figure 15:
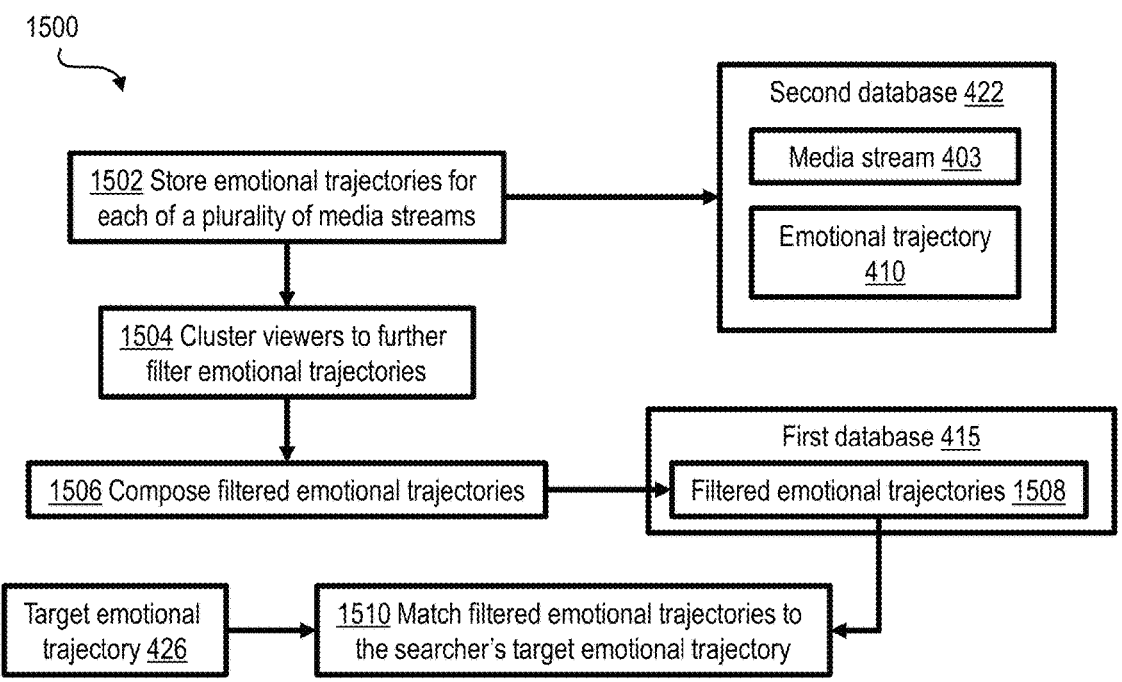
FIG. 15 depicts in a flowchart a method for emotional similarity recommendations, according to an exemplary embodiment.

FIG. 15 depicts in a flowchart a method 1500 for emotional similarity recommendations. It is noted that different people may have different emotional reactions to the same content. Thus, a combination of collaborative and emotional trajectory filtering can be used to recommend content to a searcher. According to the method 1500, at 1502 store in the second database 422 the emotional trajectory 410 of each viewer for each of a plurality of media streams 403. Using historical data of emotional trajectories in response to different media streams and reaction similarity between different viewers, at 1504 cluster the viewers to further filter emotional trajectory recommendations. At step 1504, viewers who had similar emotional trajectories in response to the same content are more closely associated with one another in the low dimensional cluster space, with a Euclidean distance metric identifying viewer similarity. Then at 1506, compose filtered emotional trajectories 1508 for each media stream only from the emotional trajectories 410 of viewers who responded to reference media streams in a similar manner to the searcher. At 1510, when matching filtered emotional trajectories 1508 from the database 415 to the searcher's target emotional trajectory 426, the matchup will be biased consistent with the searcher's reactions to previously consumed media.

Despite viewers having similar emotional reactions to the same content, an emotional prior (In Bayesian statistical inference, a prior probability distribution, often simply called the prior, of an uncertain quantity is the probability distribution that would express one's beliefs about this quantity before some evidence is taken into account), measured as the initial emotional state of a viewer at the outset of consuming a media stream, may present an emotional bias and influence the emotional trajectory for the beginning portion of the viewing session. The Bayesian approach is useful for modeling emotional state transitions: the change induced starting from a person's state (prior), given what is subsequently shown and the person's final state (posterior). Example, if a viewer's cognitive state is detected as "fragile," the measured fragility index may first have to decrease before other viewing emotions, such as joy, are experienced. This emotional prior is recorded as a feature in the recommender system and an attention-based machine learning system may differentiate emotional trajectories between former and latter parts of the viewing session (where latter trajectories have an increased likelihood of emotional influence solely from the viewing session and not the prior).

As mentioned, an aspect of the invention is training a neural network to estimate an aggregate emotional trajectory in response to a bit stream of a media stream, i.e. without actually gathering emotional response data from a plurality of viewers of the media stream. A method for doing this is described with reference to FIG. 13.

Another aspect of the invention is a method for cross domain recommendations. The idea of using emotional trajectory to make recommendations can be generalized to cross domains that are not easily associated. For example, consider a movie that is an "emotional rollercoaster" because of the numerous swings of emotion. It is possible, according to an exemplary embodiment, to recommend a music album to someone that likes this type of movie. In this instance, a conventional approach of collaborative filtering may fail because it is likely very difficult to find one database containing both movies and music preferences. In one or more embodiments, recommendations based on emotional trajectory could be used by finding a music album that elicits significant swings of emotions in the listener.

Some other examples of cross domain recommendations from emotional trajectory: life experiences (safari, tours, hikes); neighborhoods to live in; sports teams to support.

Given the discussion thus far, and with reference to the accompanying drawings, it will be appreciated that, in general terms, an exemplary method 400 for delivering electronic media content, according to an aspect of the invention, includes retrieving from an electronic database a bit stream of a media stream 403. The method also includes establishing an aggregate emotional trajectory of the media stream by, for each viewer of a plurality of viewers: at 402, rendering the bit stream to that viewer via an electronic device; at 407, establishing an emotional trajectory 410 of that viewer by, at 404, continuously measuring that viewer's emotional state, via one or more sensors 406, throughout that viewer's experience of the rendered bit stream; and, at 412, aggregating the emotional trajectories of the plurality of viewers to obtain the aggregate emotional trajectory 414 of the media stream 403. The method also includes, at 428, determining a target emotional trajectory 426 for a searcher; at 430, matching the aggregate emotional trajectory 414 of the media stream 403 to the target emotional trajectory 426 for the searcher; at 432, recommending the media stream to the searcher in response to the matching; and, at 434, rendering the bit stream of the media stream to the searcher in response to the searcher's acceptance of the recommendation.

In one or more embodiments, the one or more sensors include a video camera and the continuously measuring includes estimating each viewer's emotional state by obtaining emotive facial expressions through facial recognition and expression analysis.

In one or more embodiments, the one or more sensors include a skin conductivity sensor and the continuously measuring includes estimating each viewer's emotional state by comparing skin conductivity to a threshold value corresponding to an excited emotional state.

In one or more embodiments, the one or more sensors include a piloerection sensor and the continuously measuring includes estimating each viewer's emotional state by comparing piloerection to a threshold value corresponding to an excited emotional state.

In one or more embodiments, the one or more sensors include a heart rate monitor and the continuously measuring includes estimating each viewer's emotional state by comparing heart rate to a threshold value corresponding to an excited emotional state.

In one or more embodiments, determining the target emotional trajectory includes retrieving the searcher's reviews of previously delivered media streams, identifying positive reviews, and aggregating emotional trajectories of each media stream that the searcher has positively reviewed.

In one or more embodiments, determining the target emotional trajectory includes identifying a desirable emotional state for a the searcher, identifying a current emotional state of the searcher, and determining the target emotional trajectory that begins with the current emotional state and concludes with the desirable emotional state or desirable trajectory of emotional states.

In one or more embodiments, identifying a current emotional state includes providing the potential user with a questionnaire related to their emotional state.

In one or more embodiments, identifying a current emotional state includes monitoring a physiologic sensor attached to the searcher.

In one or more embodiments, identifying a current emotional state includes monitoring a video feed of the searcher's face and obtaining emotive facial expressions through facial recognition and expression detection processes.

According to another aspect, an exemplary method for delivering a media stream includes retrieving from an electronic database bit streams 1310 of each of a plurality of reference media streams 1314 other than the stream to be delivered, in association with aggregate emotional trajectories 414 of each of the plurality of reference media streams. The exemplary method then includes, at 1307, training a neural network classifier to produce aggregate emotional trajectories 414 of the reference media streams 1314 in response to the bit streams 1310 of the reference media streams, using the bit streams and aggregate emotional trajectories of the reference media streams as training input data and training output classifications, respectively; and inferring the aggregate emotional trajectory 1302 of the media stream 403 by retrieving from the electronic database a bit stream 1306 of the media stream and then providing the bit stream of the media stream as input to the trained neural network classifier 1308. The exemplary method also includes obtaining a target emotional trajectory 426 of a searcher (e.g., at 1104, 1108, or 1112); at 1106, matching the target emotional trajectory 426 to the aggregate emotional trajectory 1302 of the media stream 403; at 1114, recommending the media stream 403 to the searcher in response to the matching; and, at 1118, rendering the bit stream 1306 of the media stream to the searcher in response to the searcher's acceptance of the recommendation at 1116.

In one or more embodiments, obtaining the target emotional trajectory includes identifying a current emotional state of the searcher by continuously measuring signals from one or more sensors addressed to the searcher.

In one or more embodiments, the one or more sensors include a video camera and the continuously measuring includes estimating the searcher's current emotional state by obtaining emotive facial expressions through facial recognition and expression detection processes.

In one or more embodiments, the one or more sensors include a skin conductivity sensor and the continuously measuring includes estimating the searcher's current emotional state by comparing skin conductivity to a threshold value corresponding to an excited or desired emotional state.

In one or more embodiments, the one or more sensors include a piloerection sensor and the continuously measuring includes estimating the searcher's current emotional state by comparing piloerection to a threshold value corresponding to an excited or desired emotional state.

In one or more embodiments, the one or more sensors include a heart rate monitor and the continuously measuring includes estimating the searcher's current emotional state by comparing heart rate to a threshold value corresponding to an excited emotional state.

In one or more embodiments, obtaining the target emotional trajectory includes retrieving the searcher's reviews of previously delivered media streams, identifying positive reviews, and aggregating emotional trajectories of each media stream that the searcher has positively reviewed.

In one or more embodiments, obtaining of the target emotional trajectory includes identifying a desirable emotional state for the searcher, identifying a current emotional state of the searcher, and determining the target emotional trajectory that begins with the current emotional state and concludes with the desirable emotional state.

In one or more embodiments, identifying a current emotional state includes providing the searcher with a questionnaire related to their emotional state.

According to another aspect, an exemplary method for delivering a media stream includes, at 1112, identifying a desirable emotional state for a searcher; at 1112, identifying a current emotional state of the searcher; and estimating, at 428, a target emotional trajectory that begins with the current emotional state and concludes with the desirable emotional state. The method also includes step 1106 of matching the target emotional trajectory to an aggregate emotional trajectory of the media stream; step 1114 recommending the media stream to the searcher in response to the matching; and, at 1118, rendering a bit stream of the media stream to the searcher in response to the searcher's acceptance of the recommendation at 1116.

Figure 16:
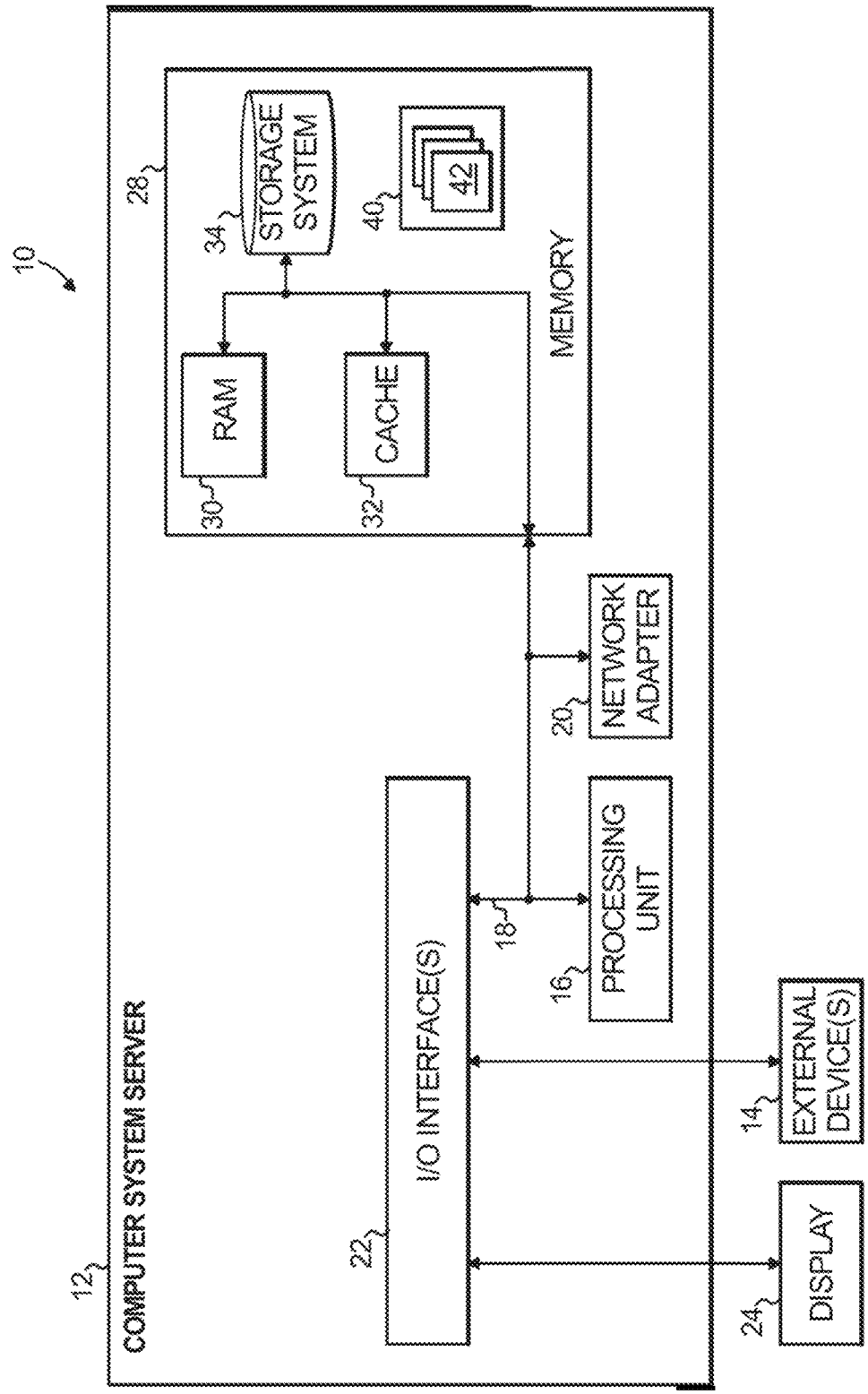
FIG. 16 depicts a computer system that may be useful in implementing one or more aspects and/or elements of the invention.

One or more embodiments of the invention, or elements thereof, can be implemented in the form of an apparatus including a memory and at least one processor that is coupled to the memory and operative to facilitate exemplary method steps, or in the form of a non-transitory computer readable medium embodying computer executable instructions which when executed by a computer cause the computer to facilitate exemplary method steps. FIG. 16 depicts a computer apparatus 10 that may be useful in implementing one or more aspects and/or elements of the invention. The computing apparatus 10 is only one example of a suitable computing apparatus and is not intended to suggest any limitation as to the scope of use or functionality of embodiments of the invention described herein. Regardless, computing apparatus 10 is capable of being implemented and/or performing any of the functionality set forth hereinabove.

In computing apparatus 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 16, computer system/server 12 in computing apparatus 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein. For example, the program modules 42 may include the first database 415, the second database 422, the emotion monitoring module 602, the aggregator module 604, the indexing module 606, the matching module 608, the recommendation module 610, and the content delivery module 612. As such, the program modules 42 in coordination with the processor 16 may implement the neural network 1308 as a part of the aggregator module 604.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 16, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 16) running a server program. It will be understood that such a physical server may or may not include a display and keyboard.

One or more embodiments can be at least partially implemented in the context of a cloud or virtual machine environment, although this is exemplary and non-limiting.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for delivering electronic media content, comprising:
    retrieving from an electronic database a bit stream of a media stream;
    establishing an aggregate emotional trajectory of the media stream by, for each viewer of a plurality of viewers:
        rendering the bit stream to that viewer via an electronic device;
        establishing an emotional trajectory of that viewer by continuously measuring that viewer's emotional state, via one or more sensors, throughout that viewer's experience of the rendered bit stream, wherein an emotional trajectory is a sequence of emotional states that are demonstrated by that viewer; and
    aggregating the emotional trajectories of the plurality of viewers to obtain the aggregate emotional trajectory of the media stream;
    determining a target emotional trajectory for a searcher;
    matching the aggregate emotional trajectory of the media stream to the target emotional trajectory for the searcher, wherein the matching is accomplished using a vector algorithm that seeks minimum distance on a Plutchik emotion wheel from each point of the target emotional trajectory to each corresponding point of the aggregate emotional trajectory of the media stream, wherein each point corresponds to an intensity of the dominant emotion at a given time;
    recommending the media stream to the searcher in response to the matching; and
    rendering the bit stream of the media stream to the searcher in response to the searcher's acceptance of the recommendation.

2. The method of claim 1 wherein the one or more sensors comprise a video camera and the continuously measuring comprises estimating each viewer's emotional state by obtaining emotive facial expressions through facial recognition and expression detection processes.

3. The method of claim 1 wherein the one or more sensors comprise a skin conductivity sensor and the continuously measuring comprises estimating each viewer's emotional state by comparing skin conductivity to a threshold value corresponding to an excited emotional state.

4. The method of claim 1 wherein the one or more sensors comprise a piloerection sensor and the continuously measuring comprises estimating each viewer's emotional state by comparing piloerection to a threshold value corresponding to an excited emotional state.

5. The method of claim 1 wherein the one or more sensors comprise a heart rate monitor and the continuously measuring comprises estimating each viewer's emotional state by comparing heart rate to a threshold value corresponding to an excited emotional state.

6. The method of claim 1 wherein the determining of the target emotional trajectory comprises identifying a desirable emotional state for the searcher, identifying a current emotional state of the searcher, and determining the target emotional trajectory that begins with the current emotional state and concludes with the desirable emotional state.

7. The method of claim 6 wherein the identifying a current emotional state comprises providing the potential user with a questionnaire related to their emotional state.

8. The method of claim 6 wherein the identifying a current emotional state comprises monitoring a physiologic sensor attached to the searcher.

9. A method for delivering a media stream, comprising:
    retrieving from an electronic database bit streams of each of a plurality of reference media streams other than the stream to be delivered, in association with aggregate emotional trajectories of each of the plurality of reference media streams wherein an emotional trajectory is a sequence of emotional states that are demonstrated by a viewer in response to a media stream;
    training a neural network classifier to produce aggregate emotional trajectories of the reference media streams in response to bit streams of the reference media streams, using the bit streams and aggregate emotional trajectories of the reference media streams as training input data and training output classifications, respectively;

inferring the aggregate emotional trajectory of the media stream by retrieving from the electronic database a bit stream of the media stream and then providing the bit stream of the media stream as input to the trained neural network classifier;

obtaining a target emotional trajectory of a searcher;

matching the target emotional trajectory to the aggregate emotional trajectory of the media stream, wherein the matching is accomplished using a vector algorithm that seeks minimum distance on a Plutchik emotion wheel from each point of the target emotional trajectory to each corresponding point of the aggregate emotional trajectory of the media stream, wherein each point corresponds to an intensity of the dominant emotion at a given time;

recommending the media stream to the searcher in response to the matching; and rendering the bit stream of the media stream to the searcher in response to the searcher's acceptance of the recommendation.

10. The method of claim 9 wherein obtaining the target emotional trajectory includes identifying a current emotional state of the searcher by continuously measuring signals from one or more sensors addressed to the searcher.

11. The method of claim 10 wherein the one or more sensors comprise a video camera and the continuously measuring comprises estimating the searcher's current emotional state by obtaining emotive facial expressions through facial recognition and expression detection processes.

12. The method of claim 10 wherein the one or more sensors comprise a skin conductivity sensor and the continuously measuring comprises estimating the searcher's current emotional state by comparing skin conductivity to a threshold value corresponding to an excited emotional state.

13. The method of claim 10 wherein the one or more sensors comprise a piloerection sensor and the continuously measuring comprises estimating the searcher's current emotional state by comparing piloerection to a threshold value corresponding to a desired emotional state.

14. The method of claim 10 wherein the one or more sensors comprise a heart rate monitor and the continuously measuring comprises estimating the searcher's current emotional state by comparing heart rate to a threshold value corresponding to a desired emotional state.

15. The method of claim 9 wherein the obtaining of the target emotional trajectory comprises identifying a desirable emotional state for the searcher, identifying a current emotional state of the searcher, and determining the target emotional trajectory that begins with the current emotional state and concludes with the desirable emotional state.

16. The method of claim 15 wherein the identifying a current emotional state comprises providing the searcher with a questionnaire related to their emotional state.

17. A method for delivering a media stream, comprising:
identifying a current emotional state for a searcher;
identifying a desirable emotional state of the searcher;
estimating a target emotional trajectory, which begins with the current emotional state and concludes with the desirable emotional state, wherein an emotional trajectory is a sequence of emotional states;
matching the target emotional trajectory to an aggregate emotional trajectory of the media stream, wherein the matching is accomplished using a vector algorithm that seeks minimum distance on a Plutchik emotion wheel from each point of the target emotional trajectory to each corresponding point of the aggregate emotional trajectory of the media stream, wherein each point corresponds to an intensity of the dominant emotion at a given time;
recommending the media stream to the searcher in response to the matching; and
rendering a bit stream of the media stream to the searcher in response to the searcher's acceptance of the recommendation.

18. The method of claim 1, wherein an emotional state is a signal that combines the intensities of eight basic emotions.

19. The method of claim 1, wherein determining the target emotional trajectory for the searcher is done by retrieving the searcher's reviews of previously delivered media streams, identifying positive reviews, and aggregating emotional trajectories of each media stream that the searcher has positively reviewed.

20. The method of claim 1, wherein determining the target emotional trajectory for the searcher is done by receiving the searcher's selection from a menu of desired emotional experiences.

* * * * *